United States Patent
Dirkzwager et al.

(10) Patent No.: US 6,861,450 B2
(45) Date of Patent: Mar. 1, 2005

(54) PROCESS FOR THE PREPARATION OF A HIGHLY LINEAR ALCOHOL COMPOSITION

(75) Inventors: Hendrik Dirkzwager, Amsterdam (NL); Laurent Alain Fenouil, Houston, TX (US); Joannes Ignatius Geijsel, The Hague (NL); Arend Hoek, Amsterdam (NL); Frederik Hendrik Van Der Steen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 74 days.

(21) Appl. No.: 10/621,816

(22) Filed: Jul. 17, 2003

(65) Prior Publication Data

US 2004/0019124 A1 Jan. 29, 2004

Related U.S. Application Data

(62) Division of application No. 10/167,209, filed on Jun. 11, 2002, now Pat. No. 6,657,092.

(30) Foreign Application Priority Data

Jun. 12, 2001 (EP) .............................................. 01305087

(51) Int. Cl.$^7$ .................... A61K 31/045; A61K 31/047; A01N 31/00
(52) U.S. Cl. ........................ 514/724; 514/738; 514/739
(58) Field of Search ................................ 514/724, 738, 514/739

(56) References Cited

U.S. PATENT DOCUMENTS

| 3,239,569 A | 3/1966 | Slaugh et al. ................ 260/632 |
| 3,239,571 A | 3/1966 | Slaugh et al. ................ 260/632 |
| 3,400,163 A | 9/1968 | Mason et al. ............. 260/606.5 |
| 3,420,898 A | 1/1969 | Van Winkle et al. ....... 260/632 |
| 3,440,291 A | 4/1969 | Van Winkle et al. ....... 260/632 |
| 3,501,515 A | 3/1970 | Van Winkle ................ 260/439 |

FOREIGN PATENT DOCUMENTS

| WO | WO 97/01521 | 1/1997 | ............. C07C/1/04 |
| WO | WO 97/38956 | 10/1997 | ............. C07C/1/04 |

*Primary Examiner*—Elvis O. Price

(57) ABSTRACT

Process for the preparation of a highly linear alcohol composition is provided comprising the steps of:
(a) reacting carbon monoxide with hydrogen under Fischer-Tropsch reaction conditions in the presence of a Fischer-Tropsch catalyst comprising cobalt;
(b) separating from the product of step (a) at least one hydrocarbon fraction comprising between 10 and 50% by weight of olefins containing 6 or more carbon atoms;
(c) contacting one or more of the hydrocarbon fractions obtained in step (b) with carbon monoxide and hydrogen under hydroformylation conditions in the presence of a hydroformylation catalyst based on a source of cobalt and one or more alkyl phosphines; and
(d) recovering the alcohol composition.

2 Claims, No Drawings

PROCESS FOR THE PREPARATION OF A HIGHLY LINEAR ALCOHOL COMPOSITION

This is a division of application Ser. No. 10/167,209 filed Jun. 11, 2002, now U.S. Pat. No. 6,657,092 the entire disclosure of which is hereby incorporated by reference.

The present invention relates to a process for the preparation of an alcohol composition, more specifically to a process for preparing an alcohol composition having a high linearity.

It is known that oxo-alcohols can be prepared by hydroformylating an olefin into an oxo-aldehyde followed by hydrogenation of this oxo-aldehyde into the oxo-alcohol. Hydroformylation is typically conducted in the presence of a homogeneous catalyst which is based on a source of a transition metal, typically a metal of Group 8 (iron, ruthenium or osmium), 9 (cobalt, rhodium or iridium) or 10 (nickel, palladium or platinum) of the Periodic Table of Elements. In their catalytically active form these metals may be used with carbonyl ligands, but they can also be used as a complex with other ligands, suitably phosphorus-containing ligands. Such catalysts are commonly referred to as phosphine and/or phosphite-modified hydroformylation catalysts.

The secondary reaction, i.e. the hydrogenation of the oxo-aldehyde into the corresponding oxo-alcohol, occurs simultaneously with the actual hydroformylation reaction. Some of the homogeneous hydroformylation catalysts are sufficiently active to hydrogenate the in-situ formed oxo-aldehyde into the desired oxo-alcohol. Sometimes, however, a separate hydrofinishing step is applied in order to improve the quality of the final oxo-alcohol product in terms of its aldehyde content.

Oxo-alcohols may be very useful as plasticizers or detergents. Typically, plasticizer alcohols comprise from 7 to 11 carbon atoms, while detergent alcohols comprise from 12 to 15 carbon atoms. An important element determining the plasticizer and detergent properties of the final oxo-alcohol product is the linearity of the product. Throughout this specification the linearity of an alcohol product is defined as the weight percentage of linear primary mono-alcohols relative to the total amount of alcohols. In general, conventional oxo-processes typically produce alcohols having a linearity of 50 to 60% by weight.

The quality of the olefin feed to the hydroformylation is an important factor in relation to the final properties of the alcohol product. In particular the amount of linear mono-olefins relative to the total amount of olefins present in the feed is an important factor.

In one aspect the present invention aims to provide an optimum quality olefin feed.

International Application No. WO 97/01521 discloses a process for producing oxygenated products, typically aldehydes and alcohols, from an olefin-rich feedstock, which process comprises reacting, in a hydroformylation stage, a Fischer-Tropsch derived olefinic product with carbon monoxide and hydrogen in the presence of a catalytically effective quantity of a hydroformylation catalyst and under hydroformylation reaction conditions, to produce oxygenated products comprising aldehydes and/or alcohols. The olefin-rich feedstock typically contains from 35 to 100% by weight olefins, of which olefins 50 to 100% by weight are linear α-olefins, 0 to 60% by weight mono-methyl branched α-olefins and 0 to 10% by weight linear internal olefins. The minimum olefin content of the feeds used in the working examples is 50% by weight (Examples 9 and 10). The Fischer-Tropsch derived olefinic product is the product obtained by subjecting a synthesis gas comprising carbon monoxide and hydrogen to Fischer-Tropsch reaction conditions in the presence of an iron-based, a cobalt-based or an iron/cobalt-based Fischer-Tropsch catalyst. A clear preference is expressed for iron-based Fischer-Tropsch catalysts, which is also illustrated by the fact that in all working examples describing hydroformylation experiments the hydroformylation feed was based on the product of a Fischer-Tropsch reaction wherein a fused iron catalyst was used.

In the process according to International Application No. WO 97/01521 the feedstock to the hydroformylation reaction stage is an olefin-rich feedstock, which is obtained by reacting carbon monoxide and hydrogen in a Fischer-Tropsch reaction followed by subjecting the Fischer-Tropsch reaction product to distillation treatments. Such distillation treatments are required in order to obtain the carbon fractions with the prescribed minimum olefin content of 35% by weight.

However, the process according to WO-A-97/01521 leaves room for improvement in terms of the combination of alcohol selectivity in the hydroformylation and linearity of the alcohols produced. This is first of all illustrated by the working examples of WO-A-97/01521: in all but one examples where a Fischer-Tropsch feed is used the linearity is at the typical level, while alcohol selectivity is not optimal. In the only example reporting a very high linearity of 84% (Example 5) the alcohol selectivity is only 64%, implying that relatively many by-products are formed. The olefin conversion in this example is also relatively poor: only 68%. Secondly, it was found that when using a fused iron catalyst the resulting olefin stream is characterised by a relatively high content of branched olefins. This is not beneficial for a high linearity of the alcohol product in combination with a high alcohol selectivity. Finally, the high olefin content of the hydroformylation feed, a prerequisite according to WO-A-97/01521, implies that quite a severe distillation treatment of the Fischer-Tropsch reaction product is required.

The present invention aims to overcome these shortcomings. More specifically, the present invention aims to provide a process for producing oxo-alcohols by the hydroformylation of Fischer-Tropsch product streams, which results in highly linear alcohols in combination with a high alcohol selectivity in the hydroformylation stage, thus limiting the amount of by-products formed. The expression "selectivity" as used throughout this specification refers to the percentage of alcohol products formed relative to the amount of total products formed from the converted olefins:

$$\text{selectivity} = \frac{\text{amount alcohols formed} \times 100\%}{\text{total amount reaction products}}$$

Furthermore, in the process of the present invention very high olefin conversion rates should be attainable, while it should also not be required to use hydroformylation feeds comprising 35% by weight or more of olefins.

It was surprisingly found that by selecting specific types of catalysts in both the Fischer-Tropsch and hydroformylation stage highly linear alcohol products could be obtained at very high alcohol selectivity and conversion rates.

The present invention provides a process for the preparation of an alcohol composition comprising one or more primary mono-alcohols, at least 60% by weight of which consists of linear primary mono-alcohols containing at least 7 carbon atoms. The process contains the steps of:

(a) reacting carbon monoxide with hydrogen under Fischer-Tropsch reaction conditions in the presence of a Fischer-Tropsch catalyst comprising cobalt;

(b) separating from the product of step (a) at least one hydrocarbon fraction comprising between 10 and 50% by weight of olefins containing 6 or more carbon atoms;

(c) contacting one or more of the hydrocarbon fractions obtained in step (b) with carbon monoxide and hydrogen under hydroformylation conditions in the presence of a hydroformylation catalyst based on a source of cobalt and one or more alkyl phosphines; and (d) recovering the alcohol composition.

Accordingly, a process for the preparation of an alcohol composition is provided, comprising at least one primary mono-alcohol, at least 60% by weight of which consists of linear primary mono-alcohols containing at least 7 carbon atoms, said process comprising the steps of:

(a) reacting carbon monoxide with hydrogen under Fischer-Tropsch reaction conditions in the presence of a Fischer-Tropsch catalyst comprising cobalt;

(b) separating from the product of step (a) at least one hydrocarbon fraction comprising between 10 and 50% by weight of olefins containing 6 or more carbon atoms;

(c) contacting at least one of the hydrocarbon fractions obtained in step (b) with carbon monoxide and hydrogen under hydroformylation conditions in the presence of a hydroformylation catalyst based on a source of cobalt and one or more alkyl phosphines thereby producing a hydroformylation product stream; and (d) recovering the alcohol composition from the hydroformylation product stream.

Alcohol composition comprising C12/C13 linear primary mono-alcohols and C12/C13 iso-alcohols, wherein the weight ratio C12 linear primary alcohol to C13 linear primary alcohol is in the range of from 0.5 to 2.0.

Alcohol composition comprising C14/C15 linear primary mono-alcohols and C14/C15 iso-alcohols, wherein the weight ratio C14 linear primary alcohol to C15 linear primary alcohol is in the range of from 1.0 to 3.0.

The alcohol composition finally obtained suitably comprises at least 60% by weight, more suitably at least 65% by weight, of linear C7+ primary mono-alcohols. Preferred compositions comprise at least 65% by weight of C10+ primary mono-alcohols. Typically, the maximum chain length of linear primary mono-alcohols present in the alcohol composition will be 20 carbon atoms, more preferably 18 carbon atoms and even more preferably 16 carbon atoms. The process of the present invention has been found particularly advantageous for preparing compositions comprising one or more of C11, C12, C13 and C14 linear primary mono-alcohols as the main component(s), while alcohol compositions comprising as main components a combination of C12 and C13 primary mono-alcohols or a combination of C14 and C15 primary mono-alcohols have been found particularly useful. However, also lower alcohol compositions may be prepared, notably compositions comprising combinations of C7, C8 and/or C9 primary mono-alcohols and compositions comprising a combination of C9, C10 and/or C11 primary mono-alcohols.

In step (a) of the present process hydrocarbons are prepared by reacting carbon monoxide and hydrogen under conditions effective to produce hydrocarbons. In general, the preparation of hydrocarbons from a mixture of carbon monoxide and hydrogen at elevated temperature and pressure in the presence of a catalyst effective to produce hydrocarbons is known as the Fischer-Tropsch hydrocarbon synthesis. Catalysts used in this hydrocarbon synthesis are normally referred to as Fischer-Tropsch catalysts and usually comprise one or more metals from Groups 8, 9 and 10 of the Periodic Table of Elements, optionally together with one or more promoters, and a carrier material. In particular, iron, nickel, cobalt and ruthenium are known to be catalytically active metals for such catalyst. The Fischer-Tropsch catalyst to be used in step (a) of the present process, however, should comprise cobalt as the catalytically active metal. The catalyst also comprises a porous carrier material, in particular a refractory oxide carrier. Suitable refractory oxide carriers include, for example, alumina, silica, titania, zirconia or mixtures thereof, such as silica-alumina or physical mixtures such as silica and titania. Very suitable carriers are those comprising titania, zirconia or mixtures thereof. Titania carriers are preferred, in particular titania which has been prepared in the absence of sulphur-containing compounds. This carrier may further comprise up to 50% by weight of another refractory oxide, typically silica or alumina. More preferably, the additional refractory oxide, if present, constitutes up to 20% by weight, even more preferably up to 10% by weight, of the carrier.

Typically, the catalyst comprises 1–100 parts by weight of cobalt (calculated as element), preferably 3–60 parts by weight and more preferably 5–40 parts by weight, per 100 parts by weight of carrier. These amounts of cobalt refer to the total amount of cobalt in elemental form and can be determined by known elemental analysis techniques.

In addition to cobalt the catalyst may comprise one or more promoters. Suitable promoters include manganese, zirconium, titanium, ruthenium, platinum, vanadium, palladium and/or rhenium. The amount of promoter, if present, is typically between 0.1 and 150 parts by weight (calculated as element), for example between 0.25 and 50, more suitably between 0.5 and 20 and even more suitably between 0.5 and 10, parts by weight per 100 parts by weight of carrier.

Typically, the Fischer-Tropsch catalyst does not contain alkali or alkaline earth metals, apart from possible impurities introduced with starting materials in the preparation process of the catalysts of the present invention. Typically, the atomic ratio of alkali or alkaline earth metals to cobalt metal is less than 0.01, preferably, less than 0.005.

The Fischer-Tropsch process conditions applied in step (a) of the present process typically include a temperature in the range from about 125 to about 350° C., preferably from about 160 to about 275° C., more preferably from about 175 to about 250° C., even more preferably from about 190 to about 240° C., and especially from about 190 to about 235° C., and a pressure in the range from about 5 to about 150 bar abs. Step (a) of the present process may be operated at the pressures conventionally applied, i.e. up to about 80 bar abs., suitably up to 65 bar abs., but also higher pressures can be applied.

In a preferred embodiment of the present invention step (a) comprises reacting carbon monoxide with hydrogen at a temperature in the range of from about 125 to about 350° C. and a pressure in the range from about 5 to about 150 bar in the presence of a catalyst comprising cobalt on a carrier comprising titania. Suitably, the catalyst and process conditions in step (a) are selected such that the product obtained in this step (a) comprises in the range of from 2 to 20% by weight of a C11 to C14 hydrocarbon fraction, which hydrocarbon fraction comprises in the range of from 10 to 50% by weight based on total weight of this fraction of C11 to C14 mono-olefins. This could, for instance, be achieved by using a Fischer-Tropsch catalyst based on cobalt and titania at operating temperatures of about 175 to about 275° C. and operating pressures of from about 30 up to about 65 bar abs.

In a further preferred embodiment of the present invention the pressure applied in step (a) is at least about 40 bar, preferably at least 50 bar. A much preferred pressure range is about 50 to about 150 bar, even more preferably from about 55 to about 140 bar. Operating temperatures at these pressures may be those normally applied, but preferred operating temperatures at these pressures are in the range of from about 150 to about 250° C., more preferably from about 160 to about 230° C.

Hydrogen and carbon monoxide (synthesis gas) are typically fed to the reactor at a molar ratio in the range from 0.5 to 4, preferably from 0.5 to 3, more preferably from 0.5 to 2.5 and especially from 1.0 to 1.5. These molar ratios are preferred for the case of a fixed bed reactor.

The Fischer-Tropsch reaction step (a) may be conducted using a variety of reactor types and reaction regimes, for example a fixed bed regime, a slurry phase regime or an ebullating bed regime. It will be appreciated that the size of the catalyst particles may vary depending on the reaction regime they are intended for. It is within the normal skills of the skilled person to select the most appropriate catalyst particle size for a given reaction regime.

Further, it will be understood that the skilled person is capable to select the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity is chosen in the range from about 500 to about 2500 Nl/l/h. If it is desired to operate the hydrocarbon synthesis process with a slurry phase regime, preferably the gas hourly space velocity is chosen in the range from about 1500 to about 7500 Nl/l/h.

After carbon monoxide and hydrogen have reacted into a hydrocarbon product in step (a), in subsequent step (b) this hydrocarbon product is separated into one or more hydrocarbon fractions comprising between 10 and 50% by weight, preferably between 15 and 45% by weight, of olefins containing 6 or more carbon atoms. Very good results have also been achieved when separating the hydrocarbon in step (b) into at least one hydrocarbon fraction containing less than 35% by weight of olefins. It was found that such fraction, which has a relatively low olefin content, is also a very good feedstock for the hydroformylation in step (c) and also results in alcohol products with high linearities and excellent alcohol selectivities. Preferably the separation in step (b) involves a distillation treatment, notably fractional distillation. Conventional distillation techniques can be used.

The separation in step (b) may be effected by fractional distillation, but could also comprise a combination of distillation with another separation treatment, such as condensation and/or extraction.

In a preferred embodiment the hydrocarbon fractions recovered after fractional distillation in step (b) are the C8–C10, C11–C12 and C13–C14 fractions, each containing at most 5% by weight, but more preferably at most 2% by weight, of the neighbouring hydrocarbon fractions. Also the C6–C8 fraction is a preferred fraction, containing at most 5% by weight, but more preferably at most 2% by weight, of the neighbouring C5 and C9 hydrocarbon fractions. Each hydrocarbon fraction of carbon number n (so n being an integer of from 6 to 14) suitably contains 10 to 50% by weight, more suitably 20 to 45% by weight, of Cn-olefins. However, as already indicated hereinbefore, hydrocarbon fractions containing less than 35% by weight of olefins are also very useful. These hydrocarbon fractions can be used individually as feed to hydroformylation step (c), but two or more of these fractions may also be combined into a feed stream to the hydroformylation in step (c). The process of the present invention is particularly suitable when using C11–C12 hydrocarbon streams and C13–C14 hydrocarbon streams as feed in step (c).

In step (c) hydroformylation takes place. For the purpose of the present invention it was found very advantageous to use as a feed in step (c):

(1) a hydrocarbon stream comprising at least 30% by weight of C11 and C12 n-alkanes and from 15 to 50% by weight of linear C11 and C12 mono-olefins (i.e. including 1-olefins, 2-olefins and internal olefins), or (2) a hydrocarbon stream comprising at least 30% by weight of C13 and C14 n-alkanes and from 10 to 45% by weight of linear C13 and C14 mono-olefins.

The feed described above under (1) suitably comprises from 55 to 75% by weight of n-alkanes and from 20 to 45% by weight of linear C11 and C12 mono-olefins, at least 75% by weight and preferably at least 80% by weight of which consists of linear C11 and C12 mono-α-olefins. In addition to the n-alkanes and mono-olefins the feed may also contain relatively small amounts of other components (typically up to a total of 15% by weight, preferably less than 10% by weight and more preferably less than 7% by weight), such as alcohols, C10 and C13 n-alkanes, C13+ olefins, branched olefins and branched alkanes.

The feed described above under (2) suitably comprises from 60 to 80% by weight of n-alkanes and from 15 to 40% by weight of linear C13 and C14 mono-olefins, at least 70% by weight and preferably at least 80% by weight of which consists of linear C13 and C14 mono-α-olefins. In addition to the n-alkanes and mono-olefins the feed may also contain small amounts of other components (typically up to a total of 15% by weight, preferably less than 10% by weight and more preferably less than 8% by weight), such as alcohols, C12 and C15 n-alkanes, C15+ olefins, branched olefins and branched alkanes.

The hydroformylation catalyst used in step (c) is based on a source of cobalt and one or more alkyl phosphines, more in particular phosphorus-containing ligand modified cobalt-based catalysts. Such catalysts are known in the art and are, for instance described in U.S. Pat. Nos. 3,239,569; 3,239,571; 3,400,163; 3,420,898; 3,440,291 and 3,501,515, which are incorporated by reference herein. For the purpose of the present invention it has, however, been found particularly advantageous to use homogeneous hydroformylation catalysts comprising cobalt as the catalytically active metal in combination with either trialkyl phosphines or optionally substituted monophosphabicycloalkanes as the ligands. Particularly the substituted or unsubstituted monophosphabicycloalkanes are preferred. Accordingly, the most preferred catalysts are those based on a source of cobalt and a monophosphabicycloalkane-ligand, wherein the phosphorus atom is substituted with hydrogen or non-acetylenic hydrocarbyl of 1 to 36 carbon atoms (e.g. alkyl or aryl) and this phosphorus atom is a member of a bridge linkage without being a bridgehead atom and which monophosphabicylcoalkane has 7 to 46 carbon atoms, 7 or 8 carbon atoms of which together with the phosphorus atom being members of the bicyclic skeletal structure. Preferred monophosphabicycloalkane ligands comprise (i) an alkyl substituent of 4 to 30, more preferably 5 to 25, carbon atoms, or a phenyl substituent or hydrogen with (ii) 8 carbon atoms together with the phosphorus-atom forming the bicyclic skeletal structure. Particularly preferred ligands are 9-eicosyl-9-phosphabicyclo[4.2.1]nonane; 9-eicosyl-9-phosphabicyclo[3.3.1]nonane; 9-phenyl-9-phosphabicyclo[4.2.1]nonane and 9-phosphabicyclo[4.2.1]nonane. These ligands as well as their preparation are disclosed in U.S. Pat. No. 3,400,163, while their use in hydroformylation reactions is disclosed in U.S. Pat. No. 3,420,898, both incorporated by reference herein.

The alkyl phosphine is used in such amount that the molar ratio of alkyl phosphine to cobalt is in the range of from 0.5 to 2, preferably 0.6 to 1.8. In addition to the cobalt and the alkyl phosphine, the hydroformylation catalyst may also comprise additional components for enhancing the stability of the Co/phosphine system and/or for improving the alcohol selectivity. Suitable additional components include strong bases, such as KOH and NaOH with KOH being particularly preferred. The additional component is typically used in such amount that the molar ratio of this component to cobalt is in the range of from 0 to 1.

The hydroformylation reaction in step (c) can be carried out under conventional hydroformylation conditions. Accordingly, suitable conditions include reaction temperatures in the range of from about 100 to about 300° C., preferably from about 125 to about 250° C., and pressures from about 1 to about 300 bar, preferably from about 20 to about 150 bar. The amount of catalyst relative to the amount of olefin to be hydroformylated is not critical and may vary widely. Typical molar ratios of catalyst to olefin in the reaction mixture at any given moment during the reaction may be in the range of from 1:1000 to 10:1. A ratio of between 1:10 and 5:1 is often used. The hydroformylation may involve the use of a solvent that does not interfere substantially with the desired reaction. Such solvents include saturated liquid organic solvents like alcohols, ethers, acetonitrile, sulfolane, paraffins and many more. It is, however, preferred not to use an additional solvent, but to use the reactant stream itself as the liquid reaction medium.

The ratio of carbon monoxide to hydrogen applied in step (c) may vary widely. It is, however, preferred that the hydrogen to carbon monoxide molar ratio in step (c) is in the range of from 1.0 to 5.0, more preferably from 1.5 to 2.5.

Typically synthesis gas, i.e. a blend of carbon monoxide and hydrogen, is used, but in principle both gases may also be fed independently from each other to the hydroformylation reaction medium. Preferably, however, synthesis gas or syngas is used. Syngas is typically made by partial combustion of a petroleum feed and commercial syngas normally comprises hydrogen ($H_2$) and carbon monoxide (CO) in a $H_2$/CO molar ratio of from 1 to 2.5. Higher molar ratios up to 10.0 could also occur in syngas, e.g. syngas prepared by the watergas shift reaction, and such syngas could also be used. Accordingly, suitable syngas comprises hydrogen and carbon monoxide in a $H_2$/CO molar ratio of from about 1.0 to about 10.0, preferably from 1.0 to 5.0. A molar ratio between 1.5 and 2.5 is most preferred.

The hydroformylation step (c) may be carried out in a continuous, semi-continuous or batch mode. In case of a continuous mode of operation, the liquid hourly space velocities typically are in the range of from about 0.1 to about 10 $h^{-1}$. When operating step (c) as a batch process, reaction times may suitably vary from about 0.1 to about 10 hours or even longer.

By operating the hydroformylation step (c) as described hereinbefore alcohol selectivities of at least 90% and even of at least 92% are achieved, while at the same time the linearity of the alcohol product obtained is at least 70% by weight, suitably at least 75% by weight, for the C7–C13 mono-alcohols and at least 60% by weight, suitably at least 65% by weight for the C14–C15 alcohols. In addition, olefin conversions as high as 95% by weight or more and even 99% by weight or more are achieved.

Step (d) of the present process involves recovering of the linear mono-alcohol product from the hydroformylation reaction product. This can be achieved by methods known in the art.

In a preferred embodiment step (d) comprises the steps of a first distillative treatment, saponification, water washing treatment and a second distillative treatment. Accordingly, in this mode of operation the hydroformylation reaction product of step (c) is first subjected to a first distillative treatment, after which the alcohol product-containing fraction obtained is subjected to a saponification treatment to remove any acids and esters followed by a water washing treatment to remove the sodium salts. The water-washed product is then subjected to a second distillative treatment to remove any remaining impurities or by-products.

The first distillative treatment preferably is a treatment resulting in a top fraction containing most (i.e. more than 50% by weight, preferably at least 70% weight, more preferably at least 80% by weight) of the alcohol product formed and a bottom fraction containing heavier components together with the rest of the alcohol product formed. The bottom fraction is suitably recycled, at least partly, and again subjected to the distillative treatment. Examples of suitable distillative treatments include flashing and short path distillation, the latter treatment being particularly preferred for the purpose of the present invention. However, other distillative treatments may also be used.

The (top) fraction containing most of the alcohol product obtained from the distillative treatment is subsequently subjected to a saponification treatment in order to remove any acids and esters, mostly formate esters, present. Saponification is typically carried out by contacting the alcohol-containing fraction with an aqueous solution of a strong basic hydroxide, typically sodium hydroxide (NaOH) or sodium boron hydride ($NaBH_4$), at elevated temperature and whilst stirring. For example, saponification may be carried out by contacting the alcohol fraction with an aqueous 0.5 to 10%, suitably 1 to 5%, NaOH solution at an organic/water phase ratio of 10:1 to 1:1, suitably 8:1 to 2:1, the exact ratio depending on the estimated amount of esters and acids present. Saponification can be carried out batch-wise or continuously, whereby each alcohol fraction is normally one to three times subjected to saponification. Typical saponification temperatures are in the range of from about 40 to about 99° C., suitably from about 60 to about 95° C. Due to the stirring conditions an emulsion in normally formed, thus allowing the saponification reactions to take place. When stirring is stopped, phase separation occurs and the organic phase containing 90% by weight or more of the alcohol product is recovered for further treatment.

The organic phase recovered from the saponification is subjected to a water wash treatment to remove the sodium salts present. Typically such water washing treatment involves from one to five water washes. A water wash is typically carried out by mixing the saponification product with water and subsequently allowing phase separation to occur. The sodium salts will then be contained in the water phase. The water phase and organic (alcohol-containing) phase are then separated. Details of suitable water wash treatments are well known to those skilled in the art.

To further increase the purity of the alcohol product obtained the water washed alcohol product is subjected to a further distillative treatment to remove any components which are lighter and/or heavier than the desired alcohol products. Such "topping and tailing" treatment can be carried out using conventional distillation techniques. For instance, fractional distillation can be used, thereby collecting those fractions which meet the specifications set and possibly combining them into one or more crude alcohol fractions.

The crude alcohol product obtained may still contain residual aldehydes and hemi-acetals. Such components could be adequately removed by subjecting the alcohol product from the topping and tailing treatment to a hydrofinishing treatment. This is a hydrogenation reaction carried out under relatively mild conditions. It can be carried out by conventional hydrogenation processes, such as by passing the crude alcohol feed together with a flow of hydrogen over a bed of a suitable hydrogenation catalyst. Such catalysts are well known in the art and typically comprise a metal with hydrogenation functionality, such as nickel, palladium or platinum, on a refractory oxide support such as alumina, silica or silica-alumina. The hydrogenation temperature and hydrogen pressure may vary within wide limits and typically range respectively from about 50 to about 250° C., preferably about 100 to about 200° C., and from about 10 to about 150 bar abs., preferably about 20 to about 100 bar abs. The hydrofinished alcohol product obtained from the hydrofinishing is the final alcohol product.

In a further aspect the present invention also relates to an alcohol composition comprising
(a) 70 to 90% by weight, preferably 75 to 85% by weight, of C12 and C13 linear primary mono-alcohols
(b) 10 to 30% by weight, preferably 15 to 25% by weight, of C12 and C13 iso-alcohols
wherein the weight ratio C12 linear primary alcohol to C13 linear primary alcohol is in the range of from 0.5 to 2.0.

The expression "iso-alcohols" as used in this connection refers to the 2-methyl isomers of the primary mono-alcohols mentioned under (a).

In a final aspect the present invention also relates to an alcohol composition comprising
(a) 55 to 80% by weight, preferably 60 to 75% by weight, of C14 and C15 linear primary mono-alcohols
(b) 20 to 45% by weight, preferably 25 to 40% by weight, of C14 and C15 iso-alcohols
wherein the weight ratio C14 linear primary alcohol to C15 linear primary alcohol is in the range of from 1.0 to 3.0.

The above alcohol compositions can be obtained by the process described hereinbefore.

The invention will now be illustrated by the following examples without limiting the scope of the invention to these particular embodiments.

EXAMPLE 1

In a Fischer-Tropsch reaction stage synthesis gas containing hydrogen and carbon monoxide in a molar ratio of about 2:1 was passed over a fixed bed of activated Fischer-Tropsch catalyst extrudates at a pressure of 60 bar and a weighted average bed temperature (WABT) of 205° C. The Fischer-Tropsch catalyst was a CoMn/titania catalyst. The GHSV amounted to 800 Nl/l/h.

The reaction product was passed into a condenser operated at 60 bar and 205° C. resulting in a heavy liquid product and a gaseous product comprising all reaction products having a boiling point below 205° C. This gaseous stream was liquefied by cooling it to 15° C. and the liquid stream obtained was subsequently subjected to a number of batch fractionation treatments using a 15 tray Fischer packed distillation column. Firstly, the C6–C10 hydrocarbon fractions were removed and subsequently the C11/C12 and C13/C14 fractions were recovered. The compositions of both these fractions are given in Table 1.

TABLE 1

| Hydroformylation feeds | | |
|---|---|---|
|  | C11/C12 fraction | C13/C14 fraction |
| C9 (% w) | | |
| alcohol | 2.0 | |
| C10 (% w) | | |
| n-alkane | 0.9 | |
| alcohol | 2.0 | |
| C11 (% w) | | |
| 1-olefin | 13.4 | |
| 2-olefin | 2.9 | |
| internal olefin | 0.2 | |
| n-alkane | 32.3 | |
| alcohol | | 2.3 |
| C12 (% w) | | |
| 1-olefin | 11.9 | |
| 2-olefin | 2.2 | |
| internal olefin | 0.5 | |
| n-alkane | 29.8 | 0.9 |
| alcohol | | 1.9 |
| C13 (% w) | | |
| 1-olefin | | 10.4 |
| 2-olefin | | 3.1 |
| internal olefin | | 0.6 |
| n-alkane | 0.7 | 36.6 |
| C14 (% w) | | |
| 1-olefin | | 8.1 |
| 2-olefin | | 2.1 |
| internal olefin | | 0.7 |
| n-alkane | | 31.9 |
| C15 (% w) | | |
| 1-olefin | | 0.5 |
| n-alkane | | 0.2 |
| Total olefin (% w) | 31.1 | 25.7 |

EXAMPLE 2

The C11/C12 fraction was subjected to a hydroformylation treatment as follows.

A 1.5 litre autoclave was charged with 597.1 grams of hydroformylation feed, 9.9 grams of n-C10 alkane (as internal standard for subsequent GC analysis) and 7.3 grams of a 5.81% by weight KOH solution in 2-ethylhexanol. The autoclave was pressurized to 30 bar with synthesis gas (ratio $H_2/CO=2$) and heated to 185° C. Then 33.6 grams of a catalyst solution were injected. This catalyst solution was obtained by premixing 214.8 grams of a 70% by weight cobalt octoate solution in Shellsol 140T (a paraffinic solvent; Shellsol is a trade mark) with 221.4 grams of 9-eicosyl-9-phosphabicyclononane ligand. Accordingly, the amount of cobalt was 0.285% by weight based on total weight of reactor contents, the ligand/cobalt molar ratio was 1.2 and the K/Co molar ratio was 0.2. Immediately after injection of the catalyst solution the pressure in the autoclave was increased to 70 bar with synthesis gas (ratio $H_2/CO=2$).

After two hours the conversion of olefins was complete. During these two hours the reaction temperature rose to 196° C. The composition of the crude C12/C13 alcohol product is indicated in Table 2.

EXAMPLE 3

Example 2 was repeated except that the C13/C14 fraction was now taken as the hydroformylation feed. The amounts of the various components used were 546 grams of C13/C14 fraction, 9.1 grams of n-C10 alkane, 6.7 grams of the 5.81% by weight KOH solution in 2-ethylhexanol and 31.0 grams of the catalyst solution.

After two hours the conversion of olefins was complete. During these two hours the reaction temperature rose to 195° C. The composition of the crude C14/C15 alcohol product is also indicated in Table 2.

TABLE 2

Crude alcohol products

|  | C12/C13 alcohol | C14/C15 alcohol |
|---|---|---|
| n-alkanes (% w) | 59.1 | 68.1 |
| aldehydes (% w) | 0.1 | 0.1 |
| alcohols (% w) | | |
| n-C9—OH | 2.1 | |
| n-C10—OH | 2.0 | |
| n-C11—OH | | 2.1 |
| n-C12—OH/i-C12—OH* | 12.9/3.7 | 1.8/0.0 |
| n-C13—OH/i-C13—OH | 10.9/3.3 | |
| n-C14—OH/i-C14—OH | 0.5/0.1 | 8.4/4.6 |
| n-C15—OH/i-C15—OH | | 5.9/3.1 |
| n-C16—OH | | 0.1 |
| other (% w)** | 5.3 | 5.8 |
| linearity (% w) | 77 | 65 |
| alcohol selectivity (%) | 94 | 94 |
| Conversion (% w) | 99.8 | 99.8 |

*n-Cm—OH is a linear primary mono-alcohol having m C-atoms
i-Cm—OH is an iso-alcohol having m C-atoms
**including 2-ethylhexanol used as catalyst solvent

EXAMPLE 4

The crude alcohol products of examples 2 and 3 were worked up by the subsequent steps of wiped film evaporation, saponification of the top fractions, batch distillation treatment to remove the top and tail fractions and hydrofinishing.

Wiped film evaporation was carried out at a temperature of 110° C. (for the crude C12/C13 alcohol product) or 120° C. (for the C14/C15 crude alcohol product), a 1 mbar abs. vacuum, a cold finger temperature of 5° C., a stirrer speed of 375 rpm and a flow rate of 16 ml/min. The obtained splits in top/bottom w/w ratios were 91/9 for the crude C12/C13 alcohol product and 90/10 for the crude C14/C15 alcohol product.

The top fraction of the wiped film evaporation was saponified by contacting it at 90° C. with an aqueous 3% NaOH solution at a phase ratio organic:water of 4:1 for the crude C12/C13 alcohol product and with an aqueous 5% NaOH solution at a phase ratio organic:water of 6:1 for the crude C14/C15 alcohol product. After phase separation the organic phase was three times washed with water under similar conditions.

The saponified alcohol products were subsequently topped to remove the light by-products and tailed to remove the heavier by-products by distillative treatment using a 15 tray Fischer packed distillation column. The resulting crude C12/C13 and C14/C15 alcohol products contained respectively 84% by weight and 89% by weight of alcohol.

These crude alcohol products were then subjected to a hydrofinishing treatment by contacting the crude alcohol (at 0.8 ml/min) with hydrogen (at 5 l/h) in a trickle flow hydrogenation column containing 14 grams of a nickel/alumina hydrogenation catalyst (HTC 400 ex Crossfield) at 120° C. and a constant hydrogen pressure of 60 bar.

The yield (relative to the C11/C12 respectively C13/C14 feed to the hydroformylation reaction), composition and linearity of the finished alcohol products obtained is given in Table 3.

TABLE 3

Finished alcohol products

|  | C12/C13 alcohol | C14/C15 alcohol |
|---|---|---|
| n-alkanes (% w) | 0.2 | 0.0 |
| alcohols (% w) | | |
| n-C10—OH | 0.2 | |
| n-C11—OH | 0.6 | |
| n-C12—OH/i-C12—OH | 45.6/5.6 | 0.4/0.0 |
| n-C13—OH/i-C13—OH | 35.1/12.1 | 0.7/0.0 |
| n-C14—OH/i-C14—OH | 0.1/0.0 | 43.6/16.6 |
| n-C15—OH/i-C15—OH | | 22.3/15.3 |
| n-C16—OH | | 0.1 |
| Linearity (% w) | 81 | 66 |
| Yield (% w)* | 57 | 60 |

*Overall alcohol yield, including hydroformylation (Examples 2 and 3) and purification steps (Example 4)

We claim:
1. An alcohol composition comprising
   (a) 70 to 90% by weight of C12 and C13 linear primary mono-alcohols and
   (b) 10 to 30% by weight of C12 and C13 iso-alcohols wherein the weight ratio C12 linear primary alcohol to C13 linear primary alcohol is in the range of from 0.5 to 2.0.
2. An alcohol composition comprising
   (a) 55 to 80% by weight of C14 and C15 linear primary mono-alcohols and
   (b) 20 to 45% by weight of C14 and C15 iso-alcohols wherein the weight ratio C14 linear primary alcohol to C15 linear primary alcohol is in the range of from 1.0 to 3.0.

* * * * *